United States Patent [19]
Cabell

[11] Patent Number: 5,023,784
[45] Date of Patent: Jun. 11, 1991

[54] METHOD FOR DIAGNOSING SERUM DEFICIENCIES

[75] Inventor: Paul Cabell, Overland Park, Kans.

[73] Assignee: Doral Technical Services, Inc., Overland Park, Kans.

[21] Appl. No.: 334,315

[22] Filed: Apr. 6, 1989

[51] Int. Cl.$^5$ .............................. G06F 15/42
[52] U.S. Cl. .................... 364/413.07; 364/413.29
[58] Field of Search ............... 364/413.07, 413.90, 364/413.29

[56] References Cited

U.S. PATENT DOCUMENTS

| | | | |
|---|---|---|---|
| 4,419,365 | 12/1983 | McLachlan | 514/575 |
| 4,511,659 | 4/1985 | Matson | 436/150 |
| 4,701,407 | 10/1987 | Appel | 435/4 |

OTHER PUBLICATIONS

Shoare et al., "Aluminum and Alzheimer's Disease", *J. Nerv. Ment. Dis.*, No. 171, pp. 553–558, Sept. 1983.
My Diet Nutrition and Diet Helper, Dynacomp Inc., 178 Phillips Rd., Webster, N.Y., 14580, 1986.

*Primary Examiner*—Jerry Smith
*Assistant Examiner*—David Huntley
*Attorney, Agent, or Firm*—Hovey, Williams, Timmons & Collins

[57] ABSTRACT

A method is disclosed for quantifying the amounts of physiological metals required to eliminate aluminum from the blood serum of a human patient. The preferred method uses a computer to calculate corrective amounts of deficinet physiological metals required to restore physiological saline conductivity reduced by the presence of aluminum.

5 Claims, 1 Drawing Sheet

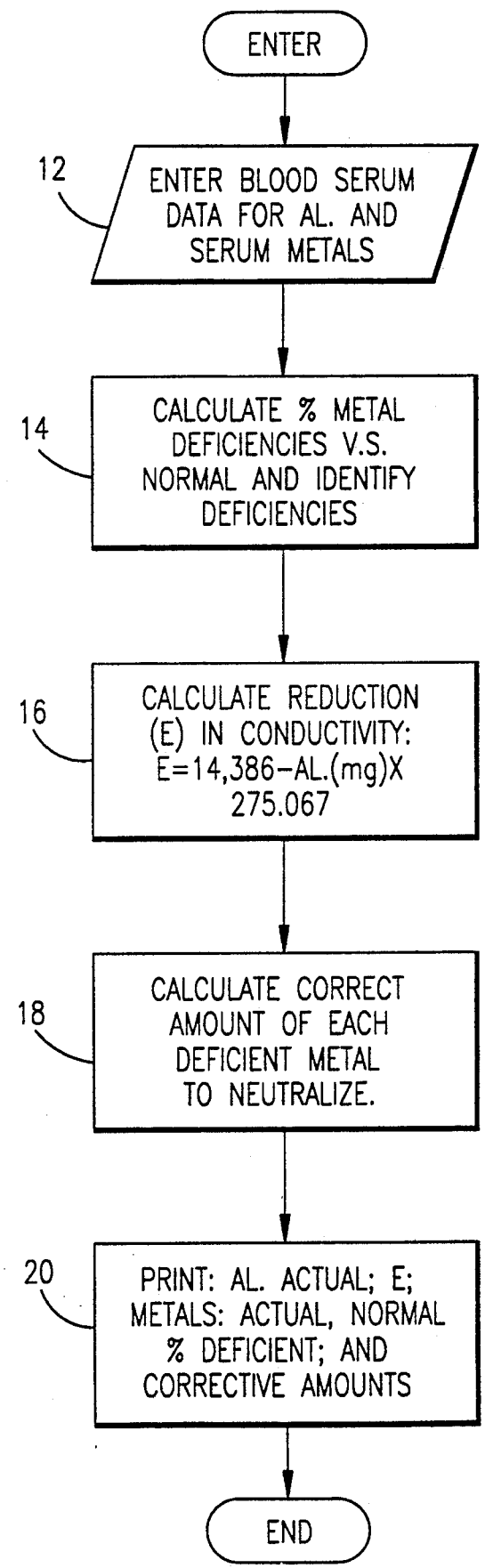

METHOD FOR DIAGNOSING SERUM DEFICIENCIES

BACKGROUND OF THE INVENTION

1. Field of the Invention

The present invention relates to a method of quantifying human blood serum deficiencies. In particular, the method hereof relates to a method of quantifying the amounts of physiological metals required to eliminate aluminum from the blood serum of a human patient.

2. Background of the Prior Art

Aluminum, usually in the form of aluminum salts such as aluminum chloride, is pervasive in the environment and is ingested by humans from the air or food. Despite the pervasiveness of aluminum in the environment, normal blood serum aluminum content is zero as set forth by the National Bureau of Standards and any amount of aluminum in blood serum is considered a risk. It has been suggested that the absence of aluminum in the blood serum, despite its pervasiveness in the environment, is due to the presence of other normally occurring physiological metals in the blood stream which are electrochemically more active than aluminum and thereby prevent its presence in the blood serum.

Medical research has indicated the presence of aluminum in the blood serum and brain cells in victims of Alzheimers disease, Parkinsons disease, and other diseases of this type. This in turn has led some researchers to speculate that a causal connection may exist between aluminum content in the blood serum and these diseases.

Because aluminum content in any amount in the blood serum is abnormal, and because of the possible causal link between blood serum aluminum and certain diseases, the prior art points out the need for a method of reducing or removing aluminum from the blood serum of human patients.

SUMMARY OF THE INVENTION

The present invention provides a method of producing and in turn eliminating aluminum from the blood serum of human patients. In this regard, the present invention encompasses a recognition that a deficiency in some physiological metals such as iron, selenium, chromium, and the like in blood serum may allow the abnormal presence of aluminum, and further recognizes that the presence of aluminum in a physiological solution of saline reduces the conductivity thereof and by quantifying such a reduction in conductivity, corrective amounts of deficient physiological metals can be determined for eliminating aluminum from the blood serum of the patient.

The method of the present invention preferably includes the step of providing a computer with data stored therein representative of the normal amounts of physiological metals which should be present in a patient's blood serum, data representative of the relationship between aluminum content and the reduction in the conductivity of physiological saline electrolyte, and the efficacy of physiological metals in restoring the reduction in conductivity. The preferred method next includes the step of analyzing a patient's blood serum for aluminum content and the physiological metals, calculating in the computer the deficiencies of the patient's blood serum of the physiological metals compared to the normal amounts, calculating the reduction in the conductivity of physiological saline as a function of the blood serum aluminum content, and calculating corrective amounts of deficient ones of the physiological metals required to restore the reduction in conductivity. It is then preferred to display the corrective amounts of the physiological metals in a usable format. Advantageously, the method also includes the step of prescribing the corrective amounts of the physiological metals as a dietary supplement up to a maximum level of the recommended daily amount of that physiological metal.

BRIEF DESCRIPTION OF THE DRAWING FIGURE

The single drawing FIGURE is a computer program flowchart of the preferred computer program for operating the computer used in the method of the present invention.

DETAILED DESCRIPTION OF THE PREFERRED EMBODIMENT

Development of the present invention recognizes that the presence of aluminum in the blood serum of a human patient is abnormal and that aluminum presence reduces the conductivity of the electrolyte associated with the blood serum. As is known, blood serum provides the electrolyte between and within neurological cells and that the presence of aluminum in the blood serum results in a corresponding presence of aluminum in the neurological cell electrolyte with a concomitant reduction in conductivity. This in turn, it is believed, reduces the efficiency of, and thereby the rate of, electrochemical activity within the brain.

Furthermore, research has indicated that the presence of aluminum in the neurological electrolyte can displace potassium ions in the neurological cells. When such occurs, the cell dies, hence, the speculation of a causal link between aluminum in human blood serum and Alzheimers-type diseases.

It is believed that normally present physiological metals in blood serum in their normal amounts electrochemically displace aluminum present in the blood serum. Thus, correction of the physiological metal deficiency in the blood serum leads to reduction of aluminum content. Quantifying the corrective amount or amounts required to restore electrolyte conductivity can be determined as a function of aluminum content in the blood serum as it affects a reduction in physiological saline conductivity.

In broad terms, the method of the present invention includes the steps of analyzing the patient's blood serum for aluminum content and quantifying this content, determining the effect of this aluminum content on the conductivity of the patient's blood serum electrolyte in accordance with the effect of this aluminum content on physiological saline, and then determining the respective amounts of physiological metals required to restore the conductivity reduction associated with the aluminum content. In this regard, the following empirical chart relates the concentration of elemental aluminum as aluminum chloride (in milligrams per milliliter) with conductivity bridge values (in micromhos per centimeter) of 50 milliliters of physiological saline:

CHART I

| Al. Content | Conductivity |
| --- | --- |
| 0 | 14,386 |
| 1 | 14,111 |
| 2 | 13,836 |
| 4 | 13,285 |
| 6 | 12,736 |

CHART I-continued

| Al. Content | Conductivity |
|---|---|
| 8 | 12,185 |
| 52 | 0 |

As can be seen from the chart, zero concentration of aluminum chloride in the saline solution illustrates a conductivity of 14,836 micromhos per centimeter (umhos/cm). At the other end of the chart, the presence of 52 milligrams aluminum produces a conductivity essentially at zero. It is believed that the effect of aluminum on physiological saline represents the effect of aluminum in human blood serum on neurological electrolyte. The chart represents selected values using the empirical formula: Conductivity (C) = 14,386 − (Al. times 275.067). After the blood serum metal content is determined, this formula can be used to quantify the reduction in saline conductivity.

The conductivity reduction can then be used to determine the amount of physiological metals required to neutralize the aluminum effect on electrolyte conductivity. The following empirically derived chart indicates the efficacy of selected physiological metals in neutralizing the conductivity reduction effect of aluminum content. As set forth, the chart indicates the amount of aluminum-caused conductivity reduction that one milligram of the elemental physiological metal will neutralize in the elemental physiological metal will neutralize in 50 milliliters of physiological saline solution.

CHART II

| Selenium | 5,800 umhos/cm |
|---|---|
| Chromium | 1,562 umhos/cm |
| Manganese | 38 umhos/cm |
| Zinc | 33 umhos/cm |
| Potassium | 31.4 umhos/cm |
| Iron | 29.3 umhos/cm |
| Sodium | 27.9 umhos/cm |
| Lithium | 26 umhos/cm |
| Magnesium | 2.2 umhos/cm |

As can be seen from the chart, selenium is the most efficacious in restoring conductivity. For example, if blood serum aluminum content of about 6.0 milligrams per milliliter is indicated from laboratory test results, a reduction of about 1,650 umhos/cm occurs in physiological saline conductivity from the norm of about 14,386 umhos/cm to 12,736 umhos/cm. Thus, a dietary supplement of chromium with an equivalence of slightly more than 1 milligram of chromium for 50 milliliters of electrolyte, for example, would neutralize the blood serum aluminum content.

It is recognized, however, that a particular prescribing physician may, in the case of a particular patient, feel that chromium is undesirable, usually because the patient is not deficient in chromium, is already high in chromium, or some other contra-indication is present. Thus, the physician may prefer instead to prescribe one of the other physiological metals such as selenium which is the most efficacious, or one of the others as a matter of medical judgment.

The physician's decision in this matter can be strongly guided by the presence of a deficiency in one of the physiological metals indicated. That is, the presence of aluminum in the blood serum indicates an electrolyte deficiency of some metal must exist to a degree sufficient to allow the aluminum to be present, and thereby produce a conductivity reduction. Accordingly, laboratory results on the physiological metals should give the physician a guide for prescribing a supplement to eliminate the deficiency. For example, if the patient has an iron deficiency, the physician may prefer to prescribe a dietary supplement of iron in the required amounts up to the maximum as determined safe and effective by the physician which would neutralize the aluminum present as well as restore a proper physiological metal balance to the patient's blood serum. The physician would normally prescribe a dietary supplement of the deficient physiological metal to restore the proper blood serum balance.

It is preferred that the method of the present invention be implemented by way of a conventional computer such as an IBM personal computer including a data entry keyboard, output display screen, output printer, and floppy disc drives for storing data and an operating program.

The single drawing FIGURE is a computer program flowchart illustrating the preferred method of implementing the present invention in the context of a personal computer. The patient's blood serum is first analyzed for aluminum and physiological metals in milligrams per milliliter. The computer program enters at step 12 in which the operator is prompted to enter the blood serum data for aluminum and physiological metals. The program then moves to step 14 which calculates the percent metal deficiency, or excess versus normal, and identifies those deficiencies. The program includes data representative of the normal amounts of physiological metals which should be present in a patient's blood serum as defined by the National Bureau Standards and others. Thus, step 14 compares the actual laboratory results entered in step 12 with these normal values and calculates a percentage deficiency or excess and identifies these deficiencies or excesses.

The program then moves to step 16 which calculates the reduction (E) in conductivity as a result of the presence of aluminum in the blood serum accordingly to the formula as shown in the drawing FIGURE.

The program then moves to step 18 which calculates a corrective amount of each physiological metal required to neutralize the conductivity reduction (E). In particularly preferred forms, the corrective amount of each of the deficient physiological metals as determined in step 14 is highlighted with an emphasis on neutralizing the aluminum effects by prescribing supplemental amounts of those physiological metals which are deficient.

The program then moves to step 20 which prints the results in a format most usable to the physician. For example, in the preferred embodiment, the printout includes the actual aluminum content of the blood serum, the resulting conductivity reduction, a chart showing the physiological metals which were analyzed, their actual values, their normal values, the percent deficiencies or excesses of each, and the corrective amounts of each physiological metal required to neutralize the conductivity reduction while highlighting the corrective amounts of deficient physiological metals. The program then ends.

EXAMPLE

In a clinical study, a patient's blood serum was analyzed for blood serum components including aluminum, lithium, magnesium, sodium, potassium, and iron among others as follows:

Aluminum: 19.9 mcg/l
Lithium: 0.0 meq/l
Magnesium: 1.8 meq/l
Sodium: 141 mEq/l
Potassium: 4.7 meq/l
Iron: 80 ug/dl Based on the aluminum content of 19.9 mcg/l, it was determined that a conductivity reduction R 8,913 umhos/cm was occurring. In response, the physician prescribed 200 micrograms of chromium and 50 micrograms of selenium in the form of a daily multivitamin supplement and placed the patient on a high lithium diet. Subsequent lab tests three months later revealed the following:

Aluminum: 10.9 mcg/l
Lithium: 0.1 meq/l
Magnesium: 1.8 meq/l
Sodium: 141 meq/l
Potassium: 4.8 meq/l
Iron: 89 ug/dl The subsequent lab results show a reduction in aluminum content from 19.9 to 10.9 mcg/l with a reported improvement in mental alertness and sleeping habits.

As those skilled in the art will appreciate, analysis of other blood components are essential to a full understanding of a patient's blood chemistry. Such things including cholesterol, creatinine, glucose, sodium, uria, uric acid, copper, cadmium, chromium, lead, vanadium, and standard enzymes are also important to a physician's understanding of the total blood chemistry of a patient. This understanding provides guidance to the physician's judgment in prescribing the physiological metals in corrective amounts for the patient.

Having thus described the preferred embodiment of the present invention, the following is claimed as new and desired to be secured by Letters Patent.

What is claimed is:

1. A method of reducing aluminum in the blood serum of a patient, said method comprising the steps of:
    taking a blood serum sample from a patient;
    analyzing said blood serum sample for the presence of aluminum and the aluminum content thereof;
    if aluminum is present in said sample, then determining the reduction in conductivity of physiological saline having the same aluminum content as said sample when aluminum presence is indicated therein;
    determining the respective amounts of physiological metals required to neutralize said conductivity reduction in said physiological saline, said amounts being representative of the respective corrective amounts of said metals needed to reduce said aluminum content in the blood serum of a patient; and
    repeatedly administering to the patient over time a dietary supplement of at least one of said physiological metals in correspondence with said amounts required to neutralize said conductivity reduction in said saline in order to reduce the aluminum in the blood serum of the patient.

2. The method as set forth in claim 1 further including the steps of:
    providing a computer having memory for storing data therein,
    storing data in said computer memory representative of normal amounts of physiological metals which should be present in a patient's blood serum,
    analyzing a blood serum sample taken from the patient for physiological metal content,
    storing in said computer memory said physiological metal content,
    retrieving from said memory said normal amounts and comparing to said physiological metal content and thereby determining which of said metals are deficient in the patient blood serum sample,
    said administering step including the step of administering said corrective amounts in accordance with deficient ones of said metals.

3. The method as set forth in claim 2 further including the steps of performing said determining steps in said computer.

4. The method as set forth in claim 1, said physiological metals including selenium, chromium, manganese, zinc, potassium, iron, sodium, lithium, and magnesium.

5. The method as set forth in claim 1, further including the step of administering said corrective amounts as a dietary supplement up to the level of the recommended daily amount of said supplement for patient.

* * * * *